(12) United States Patent
Kim et al.

(10) Patent No.: US 9,377,353 B2
(45) Date of Patent: Jun. 28, 2016

(54) OPTICAL PERSPIRATION SENSOR USING FRUSTRATED TOTAL INTERNAL REFLECTION

(71) Applicant: Intel Corporation, Santa Clara, CA (US)

(72) Inventors: Kyu Hyun Kim, Ann Arbor, CA (US); David N. Hutchison, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/318,548

(22) Filed: Jun. 27, 2014

(65) Prior Publication Data

US 2015/0377697 A1  Dec. 31, 2015

(51) Int. Cl.
*G01N 21/47* (2006.01)
*G01J 1/16* (2006.01)
*G01J 1/08* (2006.01)
*G01J 1/02* (2006.01)
*A61B 5/00* (2006.01)
*G01N 21/552* (2014.01)
*A61B 5/11* (2006.01)
*A61B 5/16* (2006.01)
*A61B 5/1455* (2006.01)

(52) U.S. Cl.
CPC .............. *G01J 1/1626* (2013.01); *A61B 5/0059* (2013.01); *A61B 5/1118* (2013.01); *A61B 5/165* (2013.01); *A61B 5/4266* (2013.01); *G01J 1/0204* (2013.01); *G01J 1/0271* (2013.01); *G01J 1/08* (2013.01); *G01N 21/552* (2013.01); *A61B 5/14551* (2013.01); *G01J 2001/0257* (2013.01); *G01J 2001/1647* (2013.01)

(58) Field of Classification Search
CPC ............. G02B 6/00; G02B 27/00; G02B 5/00; G02F 1/00
USPC ......................................................... 356/446
See application file for complete search history.

(56) References Cited

U.S. PATENT DOCUMENTS 4,484,179 A    11/1984  Kasday
5,005,005 A *   4/1991  Brossia et al. ................. 340/604
5,088,817 A *   2/1992  Igaki et al. ....................... 356/71

(Continued)

FOREIGN PATENT DOCUMENTS

JP        2006-296816 A    11/2006

OTHER PUBLICATIONS

International Search Report and Written Opinion for PCT Application No. PCT/US2015/036979 mailed Oct. 6, 2015, 13 pages.

*Primary Examiner* — Tarifur Chowdhury
*Assistant Examiner* — Isiaka Akanbi
(74) *Attorney, Agent, or Firm* — Jordan IP Law, LLC

(57) ABSTRACT

Systems and methods may provide for receiving an electrical measurement signal from a first photodetector coupled to a first waveguide and determining a total intensity level of reflected light in the first waveguide based on the electrical measurement signal. Additionally, a perspiration level of skin in contact with the first waveguide may be determined based on the total intensity level of the reflected light in the first waveguide. In one example, an electrical control signal is received from a second photodetector coupled to a second waveguide that is physically isolated from the skin, wherein the total intensity level of the reflected light in the first waveguide is determined further based on the electrical control signal.

20 Claims, 3 Drawing Sheets

(56) References Cited

U.S. PATENT DOCUMENTS

| | | | | |
|---|---|---|---|---|
| 5,165,005 A * | 11/1992 | Klainer | | G01N 21/431 356/128 |
| 7,061,619 B2 * | 6/2006 | Shirai et al. | | 356/481 |
| 7,084,980 B2 * | 8/2006 | Jones | | G01N 21/553 356/445 |
| 7,386,333 B1 * | 6/2008 | Birecki | | A61B 5/0088 600/310 |
| 7,843,571 B2 * | 11/2010 | Naya | | G01N 21/41 356/436 |
| 8,155,487 B2 * | 4/2012 | Irawan et al. | | 385/12 |
| 2007/0273867 A1 * | 11/2007 | Diessel et al. | | 356/36 |
| 2008/0212918 A1 * | 9/2008 | Babin | | 385/12 |
| 2009/0122147 A1 * | 5/2009 | Takashima | | 348/207.99 |
| 2009/0269003 A1 * | 10/2009 | Scully et al. | | 385/12 |
| 2012/0271121 A1 | 10/2012 | Torre et al. | | |
| 2013/0006080 A1 * | 1/2013 | Okada et al. | | 600/362 |
| 2014/0171759 A1 | 6/2014 | White et al. | | |

* cited by examiner

OPTICAL PERSPIRATION SENSOR USING FRUSTRATED TOTAL INTERNAL REFLECTION

TECHNICAL FIELD

Embodiments generally relate to perspiration sensors. More particularly, embodiments relate to optical sensors that use frustrated total internal reflection (fTIR) to detect perspiration.

BACKGROUND

Heartbeat sensors, blood pressure sensors, blood $O_2$ sensors, and so forth, may be integrated into portable electronic devices to facilitate health monitoring in mobile settings. Conventional perspiration sensors, on the other hand, may typically use engineered fabrics to soak and analyze sweat from the skin. Such an approach may not be practical for portable electronic devices.

BRIEF DESCRIPTION OF THE DRAWINGS

The various advantages of the embodiments will become apparent to one skilled in the art by reading the following specification and appended claims, and by referencing the following drawings, in which:

DESCRIPTION OF EMBODIMENTS

Figure 1:
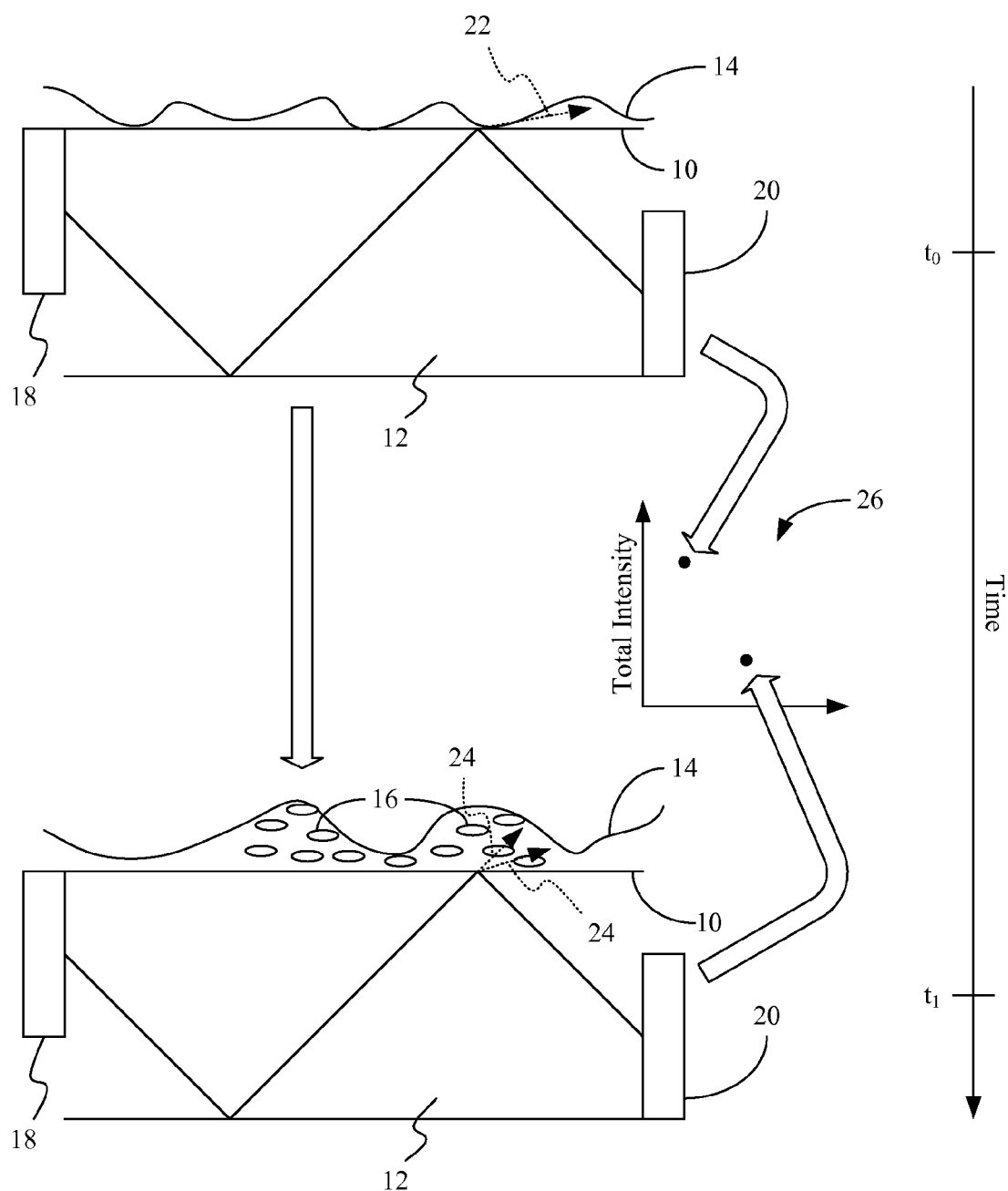
FIG. 1 is an illustration of an example of an optical perspiration sensing approach according to an embodiment.

Turning now to FIG. 1, an optical perspiration (e.g., sweat) sensing approach is shown in which a surface 10 of a waveguide 12 is exposed to the touch of the skin 14 of a user/individual. The skin 14 may be on any part of the body having external-secretory sweat glands capable of generating perspiration (e.g., due to exercise, nervousness, etc.). At time $t_0$, for example, the skin 14 may be relatively dry and at illustrated time $t_1$ the skin 14 is relatively wet due to perspiration 16. A light source 18 may be used to illuminate the waveguide 12 so that light will be internally reflected within the waveguide 12 and detected by a photodetector 20 that is optically coupled to the waveguide 12.

In general, total internal reflection (TIR) occurs in the waveguide 12 if the refractive index of the waveguide 12 is greater than the refractive index of the surrounding medium. Thus, air gaps between the skin 14 and the surface 10 of the waveguide 12 (e.g., due to ridges and valleys in a fingerprint) may lead to TIR of the light traveling in the waveguide 12 because of the lower refractive index of air. By contrast, points of contact between the skin 14 and the surface 10 of the waveguide 12 (e.g., at time $t_0$) may lead to an evanescent field that enables some optical energy 22 to escape the waveguide 12. Such a phenomenon may be referred to as frustrated total internal reflection (fTIR), wherein the escaping optical energy 22 may be scattered and/or absorbed by the skin 14.

Additionally, the presence of the perspiration 16 within the air gaps (e.g., at time $t_1$) may result in even more optical energy 24 escaping the waveguide 12. Of particular note is that the total intensity level of the reflected light in the waveguide 12 (e.g., the optical energy that does not escape) may vary depending upon the amount of perspiration 16 on the skin 14 that contacts the surface 10 of the waveguide 12. As a result, quantification results 26 of the total intensity level of reflected light may enable, for example, the wet state of the skin 14 at time $t_1$ to be automatically distinguished from the dry state of the skin 14 at time $t_0$. In addition to distinguishing between dry states and wet states, the illustrated approach may distinguish between levels of wet states (e.g., levels of perspiration). Additionally, the perspiration level may also be used to quantify exercise intensity, emotional state, and so forth.

Figure 2:
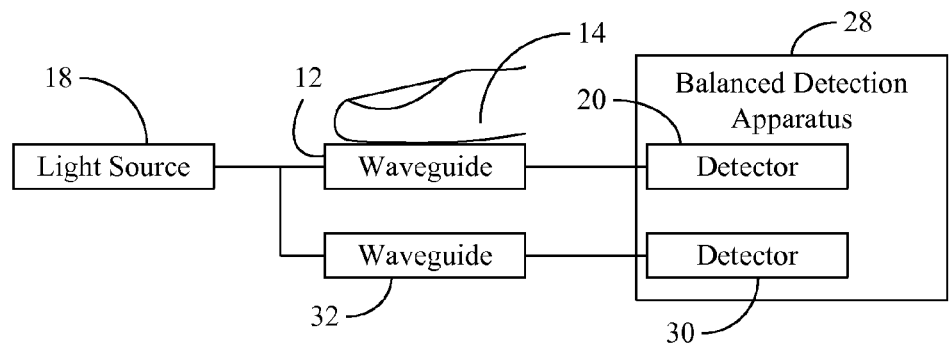
FIG. 2 is a block diagram of an example of a multi-waveguide detection configuration according to an embodiment.

FIG. 2 demonstrates that a balanced detection apparatus 28 may enable removal of noise from the intensity level measurement by using another "control" photodetector 30 (e.g., a second photodetector) to detect the total intensity level of reflected light in a control waveguide 32 (e.g., a second waveguide) that is physically isolated from the skin 14 of the user. Thus, subtracting the electrical control signal generated by the control photodetector 30 from the electrical measurement signal generated by the primary photodetector 20 may substantially improve accuracy.

Figure 3:
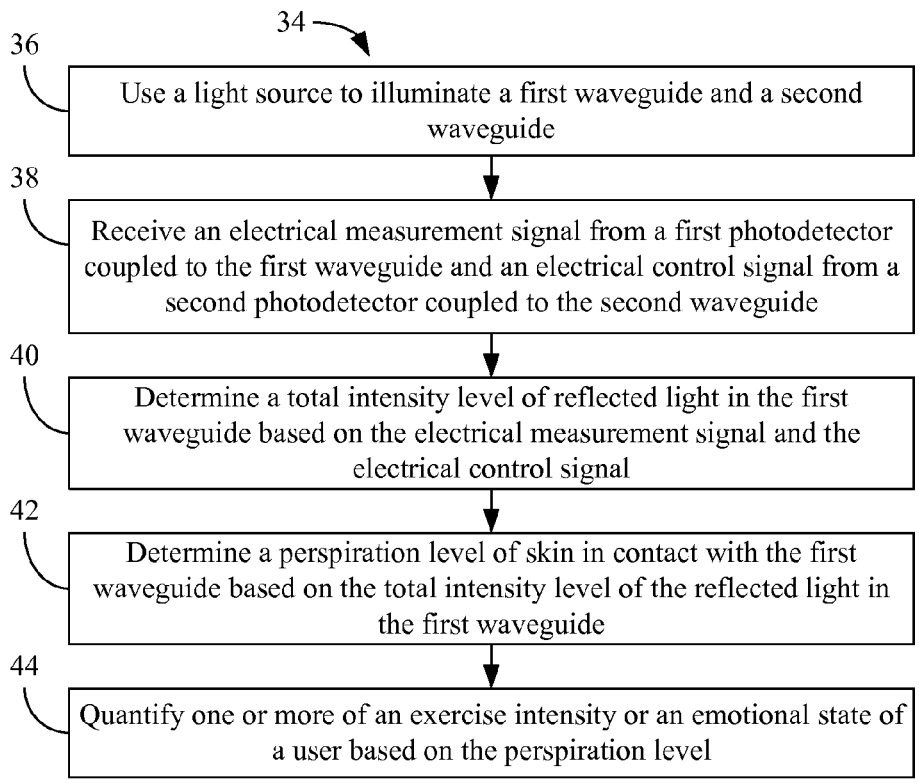
FIG. 3 is a flowchart of an example of a method of detecting perspiration according to an embodiment.

Turning now to FIG. 3, a method 34 of detecting perspiration is shown. The method 34 may be implemented as one or more modules in a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof.

Illustrated processing block 36 uses a light source to illuminate a first waveguide and optionally a second waveguide, wherein an electrical measurement signal may be received from a first photodetector coupled to the first waveguide at block 38. Block 38 may also involve receiving an electrical control signal from a second photodetector coupled to the second waveguide if the second waveguide is physically isolated from the skin of the user and a balanced detection approach such as the balanced detection apparatus 28 (FIG. 2), is used. Illustrated block 40 determines a total intensity level of reflected light in the first waveguide based on the electrical measurement signal and optionally the electrical control signal. If an electrical control signal is received, block 40 may also include subtracting the electrical control signal from the electrical measurement signal. A perspiration level of skin in contact with the first waveguide may be determined at block 42 based on the total intensity level of the reflected light in the first waveguide, wherein illustrated block 44 quantifies one or more of an exercise intensity or an emotional state of a user based on the perspiration level.

Figure 4:
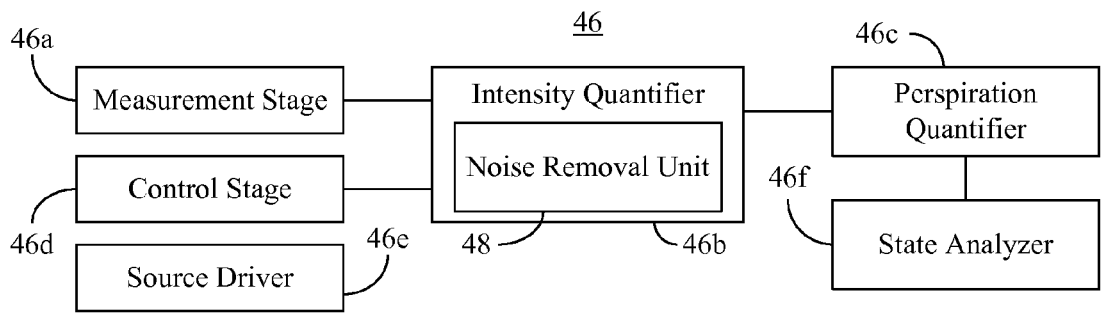
FIG. 4 is a block diagram of an example of a logic architecture according to an embodiment.

Turning now to FIG. 4, a logic architecture 46 (46a-46f) to use fTIR to detect perspiration is shown. The logic architecture 46 may generally be implemented in logic instructions, configurable logic, fixed-functionality hardware logic, etc., or any combination thereof, and may conduct one or more aspects of the method 34 (FIG. 3), already discussed. In the illustrated example, a measurement stage 46a receives an electrical measurement signal from a first photodetector coupled to a first waveguide, wherein an intensity quantifier 46b may be coupled to the measurement stage 46a. The intensity quantifier 46b may determine the total intensity level of reflected light in the first waveguide based on the electrical measurement signal. Additionally, a perspiration quantifier 46c may be coupled to the intensity quantifier 46b, wherein the perspiration quantifier 46c is configured to determine the perspiration level of skin in contact with the first waveguide based on the total intensity level of the reflected light.

In one example, the logic architecture 46 also includes a control stage 46d coupled to the intensity quantifier 46b. The control stage 46d may receive an electrical control signal from a second photodetector coupled to a second waveguide, wherein the total intensity level of the reflected light in the first waveguide may be determined further based on the electrical control signal. As already noted, the second waveguide may be physically isolated from the skin of the user. In such a case, the intensity quantifier 46b may include a noise removal unit 48 to subtract the electrical control signal from the electrical measurement signal. The logic architecture 46 may include a source driver 46e to use a light source to illuminate the first waveguide and optionally the second waveguide. Additionally, the illustrated logic architecture 46 includes a state analyzer 46f coupled to the perspiration quantifier 46c, wherein the state analyzer 46f may quantify one or more of an exercise intensity or an emotional state of a user based on the perspiration level. Thus, higher levels of perspiration may be indicative of greater amounts of exercise intensity and/or stress, depending on the individual.

Figure 5:
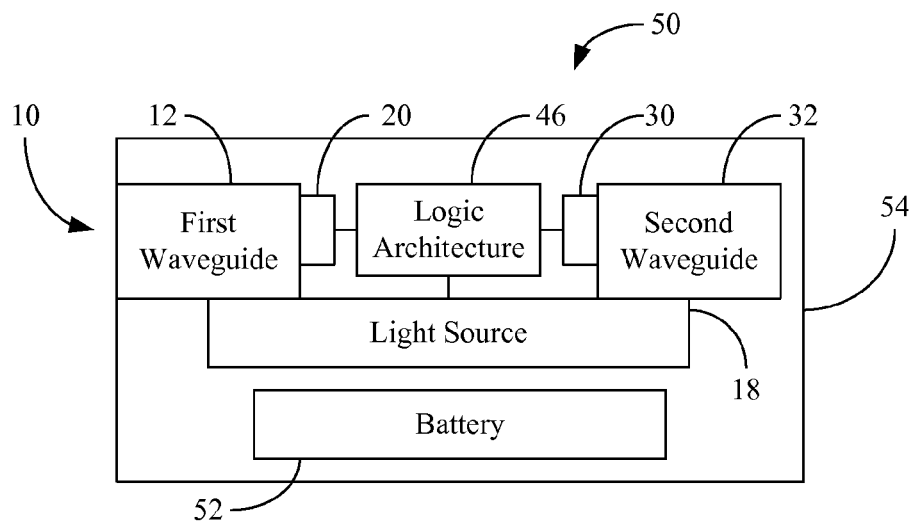
FIG. 5 is a block diagram of an example of a computing system according to an embodiment.

FIG. 5 shows a wearable computing system 50 that may be used to optically detect perspiration. In the illustrated example, the system 50 includes the first waveguide 12, the control waveguide 32, a battery 52 to supply power to the system 50 and an enclosure 54 that houses the system 50. The enclosure 54 may have a wearable form factor (e.g., headwear, eyewear, jewelry, footwear, etc., form factor) and one or more surfaces defining an aperture that exposes the surface 10 of the first waveguide 12. The control waveguide 32, on the other hand, may be physically isolated from skin that touches the surface 10 of the first waveguide 12. The first photodetector 20 may be coupled to the first waveguide 12 and the logic architecture 46 may include a measurement stage, intensity quantifier and perspiration quantifier, as already discussed.

The control photodetector 30 may be coupled to the control waveguide 32, wherein the logic architecture 46 may also include a control stage to receive an electrical control signal from the control photodetector 30 and a noise removal unit, as already discussed. The light source 18 may be used to illuminate the first waveguide 12 and the control waveguide 32.

Figure 6A:
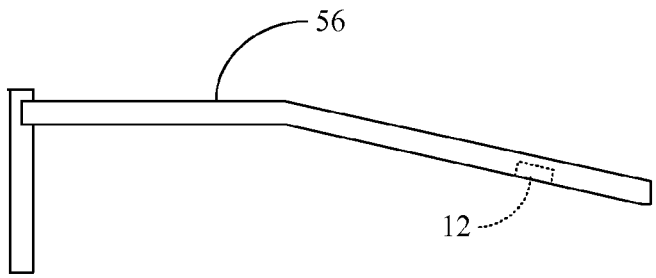
FIGS. 6A-6C are illustrations of examples of computing systems having enclosures with wearable form factors according to embodiments.
Figure 6B:
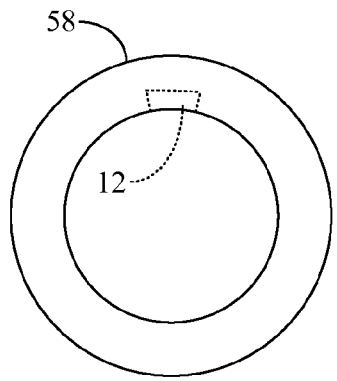
Figure 6C:
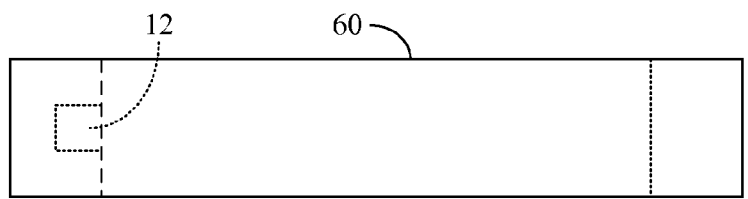

Turning now to FIGS. 6A-6C various wearable form factors are shown. More particularly, FIG. 6A demonstrates that a wearable computing system 56 may have an eyewear form factor in which a surface of the first waveguide 12 is exposed to skin behind the ear of the wearer, FIG. 6B demonstrates that a wearable computing system 58 may have a ring form factor in which a surface of the first waveguide 12 is exposed to skin on the finger of the wearer, FIG. 6C demonstrates that a wearable computing system 60 may have a headband form factor in which a surface of the first waveguide 12 is exposed to skin on the forehead of the wearer, and so forth. Other form factors such as, for example, footwear (e.g., socks), bracelets, watches, earphones, necklaces, etc., may also contain optical sensors that use fTIR to detect perspiration as described herein.

ADDITIONAL NOTES AND EXAMPLES

Example 1 may include a wearable computing system comprising a battery to supply power to the system and an enclosure that houses the system, the enclosure having a wearable form factor and surfaces defining an aperture. The system may also comprise a first waveguide, wherein the aperture of the enclosure exposes at least one surface of the first waveguide, a first photodetector coupled to the first waveguide, a measurement stage to receive an electrical measurement signal from the first photodetector, and an intensity quantifier coupled to the measurement stage, the intensity quantifier to determine a total intensity level of reflected light in the first waveguide based on the electrical measurement signal. The system may also comprise a perspiration quantifier coupled to the intensity quantifier, the perspiration quantifier to determine a perspiration level of skin in contact with the first waveguide based on the total intensity level of the reflected light.

Example 2 may include the system of Example 1, further including a second waveguide; a second photodetector coupled to the second waveguide; and a control stage coupled to the second photodetector and the intensity quantifier, the control stage to receive an electrical control signal from the second photodetector, wherein the total intensity level of the reflected light in the first waveguide is to be determined further based on the electrical control signal.

Example 3 may include the system of Example 2, wherein the intensity quantifier further includes a noise removal unit to subtract the electrical control signal from the electrical measurement signal.

Example 4 may include the system of Example 2, further including a light source coupled to the first waveguide and the second waveguide; and a source driver coupled to the light source, the source driver to use the light source to illuminate the first waveguide and the second waveguide.

Example 5 may include the system of Example 2, wherein the second waveguide is positioned within the enclosure to be physically isolated from the skin.

Example 6 may include the system of any one of Examples 1 to 5, further including a state analyzer coupled to the perspiration quantifier, the state analyzer to quantify one or more of an exercise intensity or an emotional state of a use based on the perspiration level.

Example 7 may include a method of using frustrated total internal reflection to detect perspiration, comprising receiving an electrical measurement signal from a first photodetector coupled to a first waveguide, determining a total intensity level of reflected light in the first waveguide based on the electrical measurement signal, and determining a perspiration level of skin in contact with the first waveguide based on the total intensity level of the reflected light.

Example 8 may include the method of Example 7, further including receiving an electrical control signal from a second photodetector coupled to a second waveguide, wherein the total intensity level of the reflected light in the first waveguide is determined further based on the electrical control signal.

Example 9 may include the method of Example 8, further including subtracting the electrical control signal from the electrical measurement signal.

Example 10 may include the method of Example 8, further including using a light source to illuminate the first waveguide and the second waveguide.

Example 11 may include the method of Example 8, wherein the second waveguide physically isolated from the skin.

Example 12 may include the method of any one of Examples 7 to 11, further including quantifying one or more of an exercise intensity or an emotional state of a user based on the perspiration level.

Example 13 may include at least one computer readable storage medium comprising a set of instructions which, when executed by a computing system, cause the computing system to receive an electrical measurement signal from a first photodetector coupled to a first waveguide, determine a total intensity level of reflected light in the first waveguide based on the electrical measurement signal, and determine a perspiration level of skin in contact with the first waveguide based on the total intensity level of the reflected light.

Example 14 may include the at least one computer readable storage medium of Example 13, wherein the instructions, when executed, cause a computing system to receive an electrical control signal from a second photodetector coupled to a second waveguide, wherein the total intensity level of the reflected light in the first waveguide is to be determined further based on the electrical control signal.

Example 15 may include the at least one computer readable storage medium of Example 14, wherein the instructions, when executed, cause a computing system to subtract the electrical control signal from the electrical measurement signal.

Example 16 may include the at least one computer readable storage medium of Example 14, wherein the instructions, when executed, cause a computing system to use a light source to illuminate the first waveguide and the second waveguide.

Example 17 may include the at least one computer readable storage medium of Example 14, wherein the second waveguide is to be physically isolated from the skin.

Example 18 may include the at least one computer readable storage medium of any one of Examples 13 to 17, wherein the instructions, when executed, cause a computing system to quantify one or more of an exercise intensity or an emotional state of a user based on the perspiration level.

Example 19 may include an apparatus to use frustrated total internal reflection to detect perspiration, comprising a measurement stage to receive an electrical measurement signal from a first photodetector coupled to a first waveguide, an intensity quantifier coupled to the measurement stage, the intensity quantifier to determine a total intensity level of reflected light in the first waveguide based on the electrical measurement signal, and a perspiration quantifier coupled to the intensity quantifier, the perspiration quantifier to determine a perspiration level of skin in contact with the first waveguide based on the total intensity level of the reflected light.

Example 20 may include the apparatus of Example 19, further including a control stage coupled to the intensity quantifier, the control stage to receive an electrical control signal from a second photodetector coupled to a second waveguide, wherein the total intensity level of the reflected light in the first waveguide is to be determined further based on the electrical control signal.

Example 21 may include the apparatus of Example 20, wherein the intensity quantifier further includes a noise removal unit to subtract the electrical control signal from the electrical measurement signal.

Example 22 may include the apparatus of Example 20, further including a source driver use a light source to illuminate the first waveguide and the second waveguide.

Example 23 may include the apparatus of Example 20, wherein the second waveguide is to be physically isolated from the skin.

Example 24 may include the apparatus of any one of Examples 19 to 23, further including a state analyzer coupled to the perspiration quantifier, the state analyzer to quantify one or more of an exercise intensity or an emotional state of a user based on the perspiration level.

Example 25 may include an apparatus to use frustrated total internal reflection to detect perspiration, comprising means for performing the method of any of Examples 7 to 12.

Thus, techniques may provide a dry and compact solution to detecting perspiration that does not require capturing liquid or exposing electronic components to moisture. Accordingly, the sensor may be robustly implemented into compact, portable electronics. Additionally, the techniques may be readily integrated with other health monitors (e.g., heart rate sensors, blood pressure sensors, O2 saturation sensors) into devices having light sensors, which may in turn reduce power consumption and enable smaller form factors to be achieved. Moreover, the use of light as a detection medium may enable instantaneous measurement and real-time operation.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A, B, C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A system comprising:
    a battery to supply power to the system;
    an enclosure that houses the system, the enclosure having a wearable form factor and surfaces defining an aperture;
    a first waveguide, wherein the aperture of the enclosure exposes at least one surface of the first waveguide;
    a first photodetector coupled to the first waveguide;
    a measurement stage to receive an electrical measurement signal from the first photodetector;
    a second waveguide;
    a second photodetector coupled to the second waveguide;
    a control stage coupled to the second photodetector, the control stage to receive an electrical control signal from the second photodetector;
    an intensity quantifier coupled to the measurement stage and to the control stage, the intensity quantifier to determine a total intensity level of reflected light in the first waveguide based on the electrical measurement signal and on the electrical control signal; and
    a perspiration quantifier coupled to the intensity quantifier, the perspiration quantifier to determine a perspiration level of skin in contact with the first waveguide based on the total intensity level of the reflected light.

2. The system of claim 1, wherein the intensity quantifier further includes a noise removal unit to subtract the electrical control signal from the electrical measurement signal.

3. The system of claim 1, further including:
    a light source coupled to the first waveguide and the second waveguide; and
    a source driver coupled to the light source, the source driver to use the light source to illuminate the first waveguide and the second waveguide.

4. The system of claim 1, wherein the second waveguide is positioned within the enclosure to be physically isolated from the skin.

5. The system of claim 1, further including a state analyzer coupled to the perspiration quantifier, the state analyzer to quantify one or more of an exercise intensity or an emotional state of a use based on the perspiration level.

6. A method comprising:
    receiving an electrical measurement signal from a first photodetector coupled to a first waveguide and an electrical control signal from a second photodetector coupled to a second waveguide;
    determining a total intensity level of reflected light in the first waveguide based on the electrical measurement signal and on the electrical control signal; and
    determining a perspiration level of skin in contact with the first waveguide based on the total intensity level of the reflected light.

7. The method of claim 6, further including subtracting the electrical control signal from the electrical measurement signal.

8. The method of claim 6, further including using a light source to illuminate the first waveguide and the second waveguide.

9. The method of claim 6, wherein the second waveguide is to be physically isolated from the skin.

10. The method of claim 6, further including quantifying one or more of an exercise intensity or an emotional state of a user based on the perspiration level.

11. At least one non-transitory computer readable storage medium comprising a set of instructions which, when executed by a computing system, cause the computing system to:
    receive an electrical measurement signal from a first photodetector coupled to a first waveguide and an electrical control signal from a second photodetector coupled to a second waveguide;
    determine a total intensity level of reflected light in the first waveguide based on the electrical measurement signal and on the electrical control signal; and
    determine a perspiration level of skin in contact with the first waveguide based on the total intensity level of the reflected light.

12. The at least one computer readable storage medium of claim 11, wherein the instructions, when executed, cause a computing system to subtract the electrical control signal from the electrical measurement signal.

13. The at least one computer readable storage medium of claim 11, wherein the instructions, when executed, cause a computing system to use a light source to illuminate the first waveguide and the second waveguide.

14. The at least one computer readable storage medium of claim 11, wherein the second waveguide is to be physically isolated from the skin.

15. The at least one computer readable storage medium of claim 11, wherein the instructions, when executed, cause a computing system to quantify one or more of an exercise intensity or an emotional state of a user based on the perspiration level.

16. An apparatus comprising:
    a measurement stage to receive an electrical measurement signal from a first photodetector coupled to a first waveguide;
    a control stage to receive an electrical control signal from a second photodetector coupled to a second waveguide;
    an intensity quantifier coupled to the measurement stage and to the control stage, the intensity quantifier to determine a total intensity level of reflected light in the first waveguide based on the electrical measurement signal and on the electrical control signal; and
    a perspiration quantifier coupled to the intensity quantifier, the perspiration quantifier to determine a perspiration level of skin in contact with the first waveguide based on the total intensity level of the reflected light.

17. The apparatus of claim 16, wherein the intensity quantifier further includes a noise removal unit to subtract the electrical control signal from the electrical measurement signal.

18. The apparatus of claim 16, further including a source driver use a light source to illuminate the first waveguide and the second waveguide.

19. The apparatus of claim 16, wherein the second waveguide is to be physically isolated from the skin.

20. The apparatus of claim 16, further including a state analyzer coupled to the perspiration quantifier, the state analyzer to quantify one or more of an exercise intensity or an emotional state of a user based on the perspiration level.

* * * * *